United States Patent [19]

Polcyn et al.

[11] 4,191,940
[45] Mar. 4, 1980

[54] METHOD AND APPARATUS FOR ANALYZING MICROSCOPIC SPECIMENS AND THE LIKE

[75] Inventors: Fabian C. Polcyn; Robert E. Marshall; H. Janney Nichols, all of Ann Arbor, Mich.

[73] Assignee: Environmental Research Institute of Michigan, Ann Arbor, Mich.

[21] Appl. No.: 867,979

[22] Filed: Jan. 9, 1978

[51] Int. Cl.$^2$ .................. G06K 9/00; G06M 11/00
[52] U.S. Cl. .................. 340/146.3 B; 250/226; 235/92 PC; 340/146.3 CA; 356/39; 364/416; 364/526
[58] Field of Search .................. 364/416, 526; 340/146.3 B, 146.3 CA, 146.3 AC; 250/226; 356/39, 77, 96, 179, 173; 235/92 PC

[56] References Cited

U.S. PATENT DOCUMENTS

| | | | |
|---|---|---|---|
| 3,233,219 | 2/1966 | Atrubin et al. | 340/146.3 S |
| 3,858,044 | 12/1974 | Frappe | 250/226 |
| 3,942,154 | 3/1976 | Akami et al. | 340/146.3 B |
| 3,945,729 | 3/1976 | Rosen | 250/226 |
| 3,973,725 | 8/1976 | Watanabe et al. | 364/416 |
| 4,075,604 | 2/1978 | Degasperi | 340/146.3 B |
| 4,090,243 | 5/1978 | Kotera et al. | 364/526 |
| 4,125,828 | 11/1978 | Resnick et al. | 340/146.3 CA |
| 4,127,773 | 11/1978 | West | 250/226 |

Primary Examiner—Leo H. Boudreau
Attorney, Agent, or Firm—Krass & Young

[57] ABSTRACT

To form a map of the characteristics of a microscopic specimen, the specimen is supported on a slide and a point on the specimen is subjected to either polychromatic radiation or a series of monochromatic radiations of varying wavelengths employing a condensing optical system. The resulting radiation from the point is gathered by an optical system and detected either by a single wide band detector in the case of the series of monochromatic radiations or a group of frequency selective detectors in the case of polychromatic radiation, to develop a set of signals having values which are functions of properties of the point as analyzed at the different wavelengths. The specimen is either repeatedly translated relative to the radiation source or imaged once or several times so that a signel set is derived from each elemental point on the area of the object to be analyzed in each spectral band of interest. Multi-variate statistical analysis is performed on these point sets to compare each set with one of a plurality of spectral signatures and a two dimensional map or image of the specimen area is made based on these comparisons.

18 Claims, 8 Drawing Figures

METHOD AND APPARATUS FOR ANALYZING MICROSCOPIC SPECIMENS AND THE LIKE

BACKGROUND OF THE INVENTION

1. Field of the Invention

This invention relates to methods and apparatus for analyzing the properties of microscopic specimens by detecting the radiation emanating from elemental points on an area of the object at a plurality of different wavelengths and performing statistical, multi-variate analysis on the detected sets of points to identify each with one or more of a plurality of spectral signatures.

2. Prior Art

A variety of sophisticated techniques exist for analyzing properties of microscopic specimens in general, and particularly biological specimens by measuring the radiation from the specimens at a plurality of different wavelengths. For example, experimental work has been conducted in forming a series of photograhs of microscopic specimens employing different filters with each photograph to obtain images of the object at a series of particular wavelengths of interest. These images were then combined in some manner to obtain composite mappings showing spectral differences in a single image. Another related technique employed a spectrophotometer or spectroradiometer to obtain spectra from a number of spatially separated points on an object. Microspectrophotometers are used in this manner to obtain quantitative information about cytological or hystological specimens.

The "film-filter" techniques generate useful maps which segregate the various areas of an object's surface as a function of their spectral properties. Similarly, microspectroscopic techniques may be employed to obtain information relating to the properties of a plurality of points on an object and a mapping may be prepared on that basis. However, with these techniques the problem of identifying the nature of each point based on the spectral information from the point is extremely difficult and time consuming.

Independently of consideration of these problems, over the past few years extremely powerful techniques have been developed for extracting meaningful information regarding the earth's surface by overflying the surface with aircraft or spacecraft and detecting the spectral radiance of the underlying points in a number of properly chosen spectral bands. The power of this technique lies in its ability to identify the radiation spectrum of each point with known physical materials based not only on the information from each point by itself, but also on a statistical comparison of the radiation set from each point with a plurality of previously developed spectral signatures of known classes of materials, employing statistical multi-variate analysis. When the radiation from each elemental point in a scene is sensed in a relatively large number of spectral bands, i.e., 5–25, as is often required to differentiate between similar numbers of possible materials on a statistically meaningful basis, a relatively large number of calculations are required to perform the analysis (typically about 1,000 calculations per scene point) and until recently the magnitude of these calculations presented a substantial obstacle to the use of such procedures. However, special purpose computers have now been developed to perform these calculations at rates in the range of $10^5$ points per second. As a result, it has now become practical to process an image data set from an aircraft or spacecraft at rates of about $10^7$ picture elements per minute. This has made it possible to analyze geographical features, crops, and the like, in a truly meaningful manner.

SUMMARY OF THE INVENTION

The present invention is broadly directed toward a method of employing techniques which adopt the relatively gross remote sensing techniques developed to identify the properties of earth areas to the problem of enhancing classifying and identifying the properties of microscopic specimens and biological specimens in particular. The invention is also directed toward novel apparatus for practicing this methodology.

Very broadly, the system of the present invention employs a translatable microscope stage for supporting a biological specimen. In a preferred embodiment of the invention, which will subsequently be disclosed in detail, a polychromatic optical source is passed through a condensing lens system and a spectral filter, to develop an intense illumination source that is directed at one or all target points on the specimen. An objective is used to collect the radiation which results from this illumination. The detected radiation may be based upon the absorption of the incident radiation by the specimen, stimulated radiation from the specimen as a result of the illumination or simply the resulting, reflective radiation. The collecting optical system images the object radiation on a photodetector and the resulting analog signal is converted to a digital value and stored. The filter is then changed and another measurement is made at a separate wavelength. This process is then repeated to generate a set of digital signals representative of the point radiation at a plurality of selected wavelengths. The stage is then translated and the same process is repeated for the next point. The translation process involves a rectangular scanning of the specimen so that digital data sets are derived from each elemental point in the object area under consideration.

Alternatively, each point on the object may be illuminated by a polychromatic source and the resulting radiation measured simultaneously at a plurality of different wavelengths by a group of parallel detectors all fed from the collecting optics.

After a data body consisting of a digital set of measurements representing the radiation from the object point at a plurality of separated wavelengths has been derived for each elemental point in the area, this data body is processed on a multi-variate statistical basis to determine the optimum comparison of each set with a plurality of previously derived spectral signatures, each of which is identified with a material of known physical and/or chemical characteristics. These signatures are derived previous to the statistical processing of the data body by the detection of radiation from known materials or identifiable points on the specimen.

In the preferred embodiment of the invention this processing is performed by a parallel, multi-channel, pipeline digital processor which will be subsequently disclosed in greater detail.

The method and apparatus of the present invention has utility for a variety of specific microscopic applications. One of these is improving the efficiency of present methods of analysis of stained biological specimens. For example, highly effective present stains require relatively long processing times. Using the method and apparatus of the present invention less effective stains requiring lesser processing times will become more effective and adequate for a quality of cytological or hystological analysis which is not presently possible. Similarly, the analysis of the contrasts obtainable with presently used stains can be substantially increased and the precision of assay improved.

Other objectives, advantages and applications of the present invention will be made apparent by the following detailed description of a preferred embodiment of the invention. The description makes reference to the accompanying drawings in which.

Figures 4A, 4B:
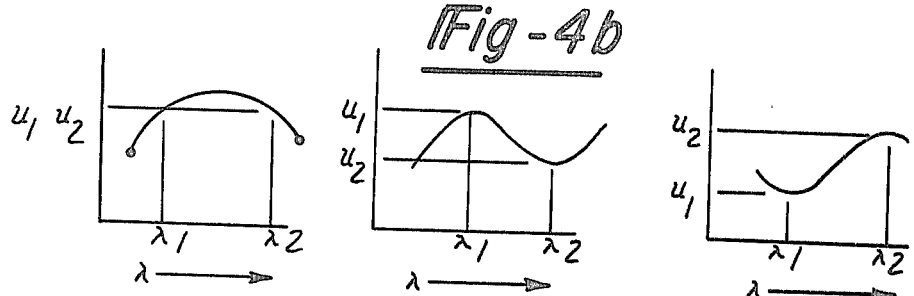
Figure 4C:
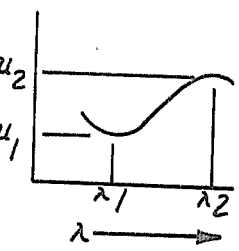
Figure 5:
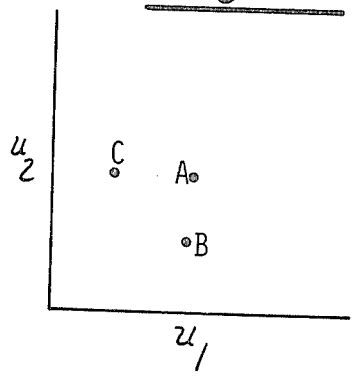
Figure 6:
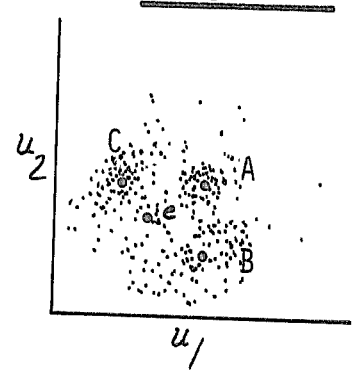
Figure 7:
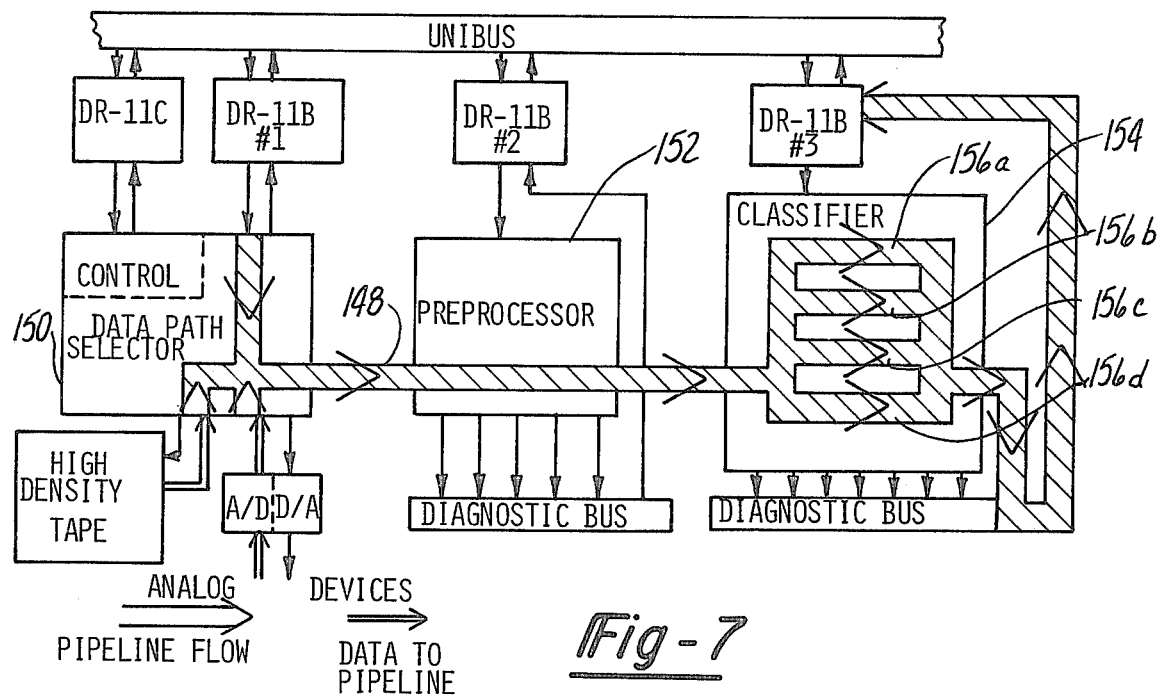

FIGS. 4a, b and c are spectral curves and scanner responses for three materials analyzed at two wavelengths;

FIG. 5 is a plot of the responses for the three materials illustrated in FIG. 4;

FIG. 6 is a plot of the responses of a large number of samples of the three materials illustrated in FIG. 4;

FIG. 7 is a block diagram showing the organization of the system; and

Figure 8:
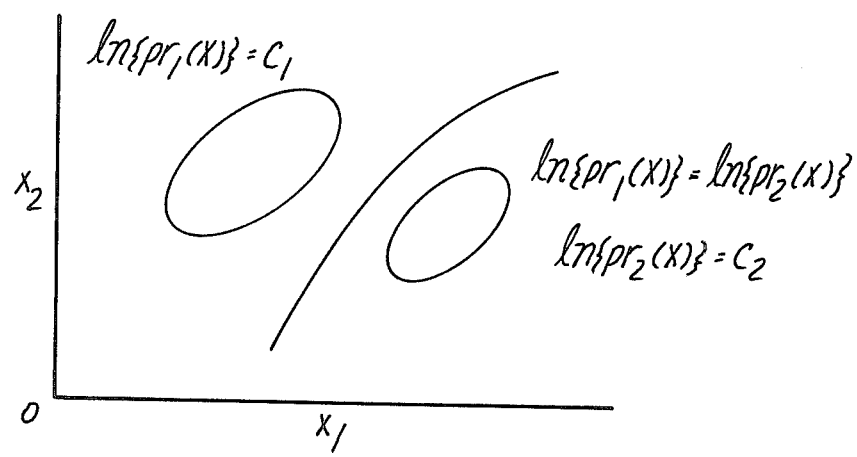

FIG. 8 is a diagram illustrating a geometric interpretation of the decision process employed in the system.

A broad method of the present invention may be considered as incorporating two separate phases: a data collecting phase wherein an area of a microscopic specimen is analyzed on a point-to-point basis at a plurality of wavelengths of interest to derive a data set for each point consisting of a numerical index of the property under investigation at each of the wavelengths; and secondly a processing step wherein all of the data sets are processed on a multi-variate statistical basis to determine optimum comparison of each set with a plurality of previously derived spectral signatures. Considering first the problem of deriving the data set for each point, FIG. 1 discloses a preferred embodiment of apparatus for deriving such sets.

A specimen to be analyzed is prepared in a conventional manner for microscopic analysis on a slide 10 including appropriate staining or the like. The slide 10 is supported on a stage 12 having a central rectangular aperture 14 so that the area on the slide to be analyzed is disposed over the aperture. The stage 12 is supported for movement along two mutually perpendicular axes lying in the plane of the stage support surface. Motion along one axis is powered by a digital stepping motor 16 which rotates a lead screw 18 to translate the stage 12 along guides 20. Motion along the other axis is powered by a digital stepping motor 22 which drives a lead screw 24 to move the stage 12 and the slide assembly 20 along guides 26.

The radiation used to analyze the specimen is derived from a light source 28. The source is preferably a set of laser generated wavelengths. The source is alternatively a Xenon arc lamp which provides a broad band of radiation including most frequencies which would be of interest. The light from the lamp 28 is passed through a pinhole 30 and a collimating lens 32. The collimated output of the lens 32 is directed through one of the sections of a rotatable filter wheel 34 having one pass filter section for each wavelength to be used in examination of the specimen. The rotational position of the filter wheel 34 is controlled by a drive motor 36. Rotation of the filter wheel changes the filter through which the output beam from the condensing lens 32 is passed.

The filtered light beam is reflected by a mirror 38 to a reflecting condenser 40 which collects and focuses the light on an elemental point or area on the specimen slide 10.

A reflecting objective 42 is supported on the opposite side of the slide 10 from the condenser 40 and receives radiation from the point on the slide under examination. The objective 42 collects the radiation and passes it to a half-silvered mirror 44. The mirror reflects a small portion of the radiation to an eyepiece 36 allowing visual examination of the point under analysis. The major portion of the output beam from objective 42 is reflected by a mirror 46 to some form of photodetector 48. In a preferred embodiment of the invention the photodetector 48 will take the form of a silicon photodetector. Other forms of photodetectors and photomultipliers could be employed.

A gate 50 receives the output of the photodetector 48 and provides it to a memory 52 under the direction of a digital control system 54. The control system specifies the memory location within the memory 52 where a particular output from the photodetector 48 is to be stored. The control 54 also provides appropriate outputs to the stage drive motors 16 and 22 and to the filter wheel drive motor 36. It thus controls the point on the slide 10 which is disposed in the incident radiation and the wavelength of the radiation.

In use, the control 54 drives the stage motors 16 and 22 to an appropriate point and then causes the electrical measurement of the collected radiation to be stored at an appropriate location with the memory 52. The control then rotates the filter wheel 34 to change the wavelength of the radiation which impinges upon the slide point under examination. The resulting photodetector value is stored at another location and this process is continued until the point has been examined with each wavelength of interest. Then the stage motors are controlled to move the next point into examination position. This process is continued until the entire area of the specimen to be mapped has been examined. The memory 52 will then contain a set of data values for each incremental point on the specimen.

Systems are commercially available which include a Vidicon, memory, gating, control and power supply electronics. The "Optical Multi-Channel Analyzer (OMA)" manufactured by Princeton Applied Research Company, Princeton, N.J., is well suited to this use. Radiation values may be stored on the Vidicon in this system to speed the examination process.

Figure 1:
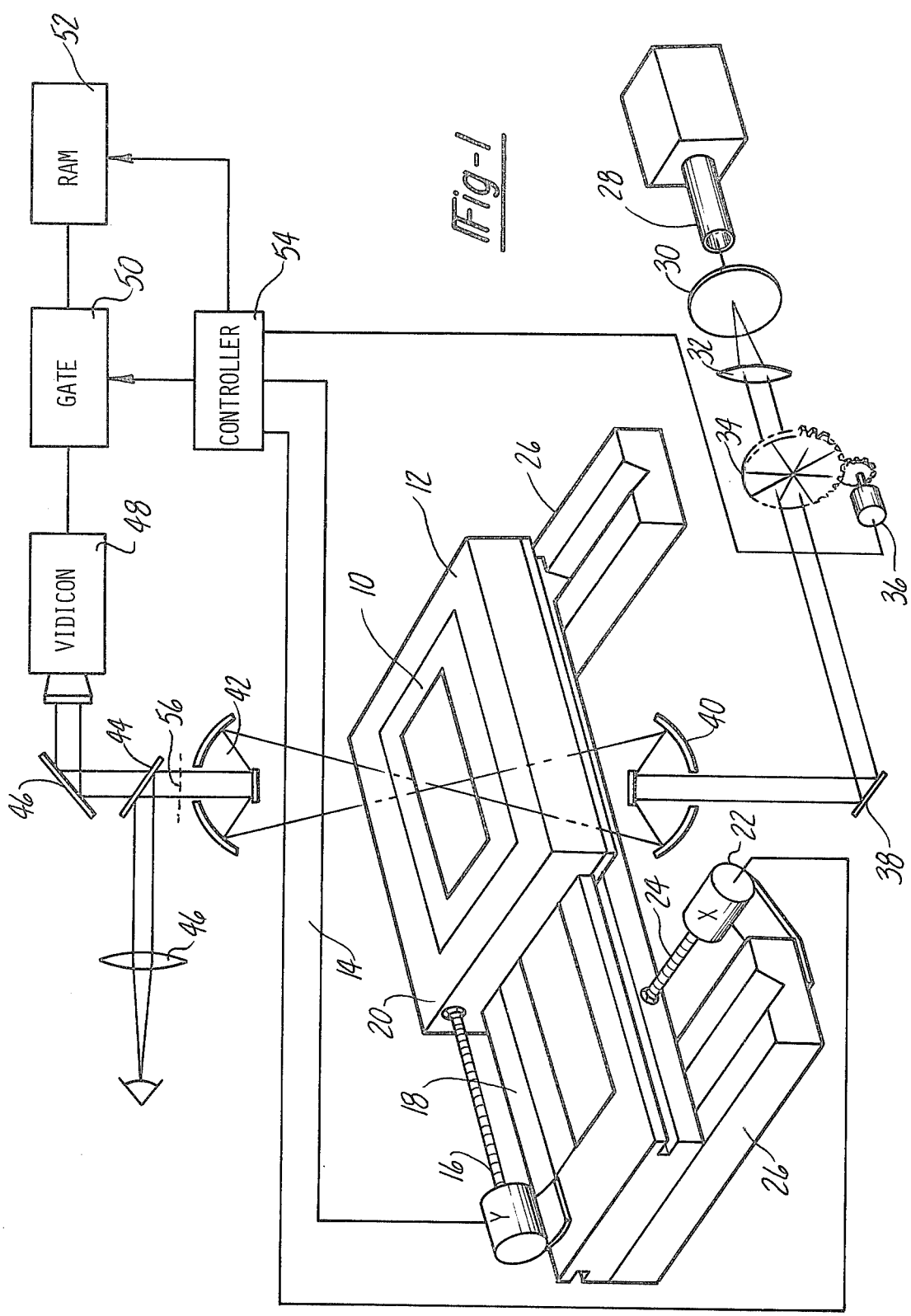
FIG. 1 is a partially schematic, partially block diagram of a first embodiment of a microscope for analyzing the radiation from points on a microscopic specimen at a plurality of wavelengths.

If the system of FIG. 1 were to be used to direct the stimulated radiation of the point under examination, such as its fluorescent properties, it would be necessary to impose an appropriate filter in the detection path, this filter is illustrated in FIG. 1.

Figure 2:
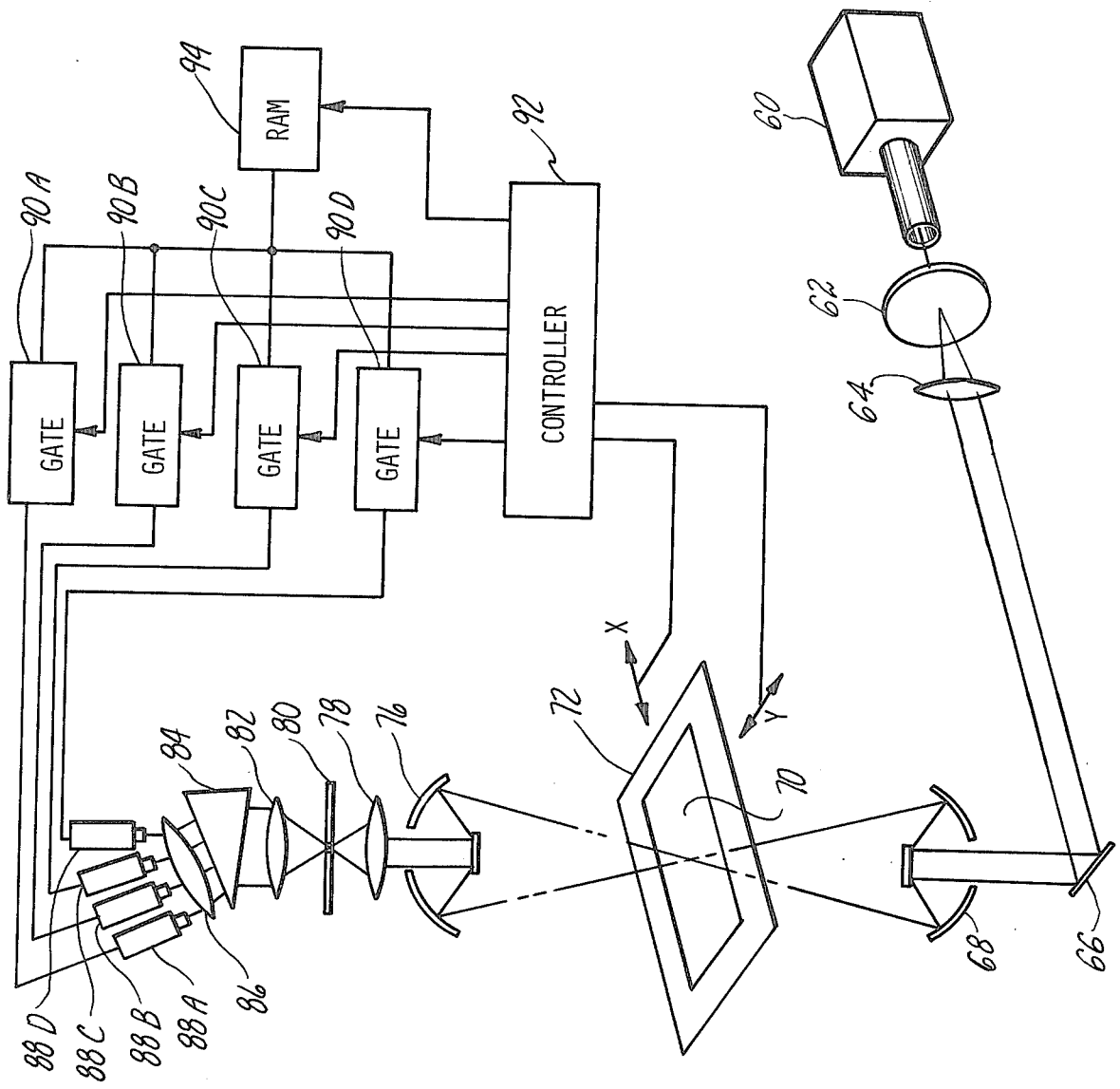
FIG. 2 is a partially schematic, partially block diagram of an alternative embodiment of microscopic multi-spectral apparatus.

An alternative embodiment of a device for deriving a data set representative of the radiation properties of each elemental point in an area under examination on a microscopic specimen is schematically illustrated in FIG. 2. Radiation from a broad spectrum source such as an Xenon lamp 60 is passed through a spatial filter consisting of a pinhole 62 and a collimating lens 64. A mirror 66 reflects the collimated illumination to a reflecting condenser 68 which focuses the broad band radiation on an elemental point of a slide 70 supported on a suitable two axis translating stage 72. The resulting illumination from the elemental point on the slide 70 is collected by a reflecting objective 76. A lens 78 focuses the collected radiation on a spectrometer entrance slit 80, and a collimating objective 82 directs the beam to a dispersing element 84. A reimaging lens 86 directs the dispersed wavelengths of the beam onto a plurality of photodetectors 88a, 88b, 88c and 88d. One photodetector may be provided for each wavelength of interest.

The outputs of the photomultipliers 88a through 88d are provided to a series of companion gates 90a–90d which may be selectively enabled by outputs from the control system 92. The outputs of the gates are provided to a memory 94 and are stored in the memory at locations specified by the control system 92. The control system also provides outputs to x and y coordinate drive motors for the stage 72.

Employing this system, an elemental point on the slide 72 is illuminated and the resulting radiation output from the point is collected at four different wavelengths by the photodetectors 88a–88d. The positions of the photodetectors with respect to the prism 84 and the reimaging lens 86 control the wavelengths that are examined. Photodetectors could be adjustably spaced with respect to the dispersive system so that the wavelengths under examination can be controlled. After the outputs of the photodetectors 88 are stored within the memory 94 the control system causes the stage 72 to move to bring the next elemental point in the area under examination. This is continued until a data set has been derived and stored for each elemental point in the area of examination.

Figure 3:
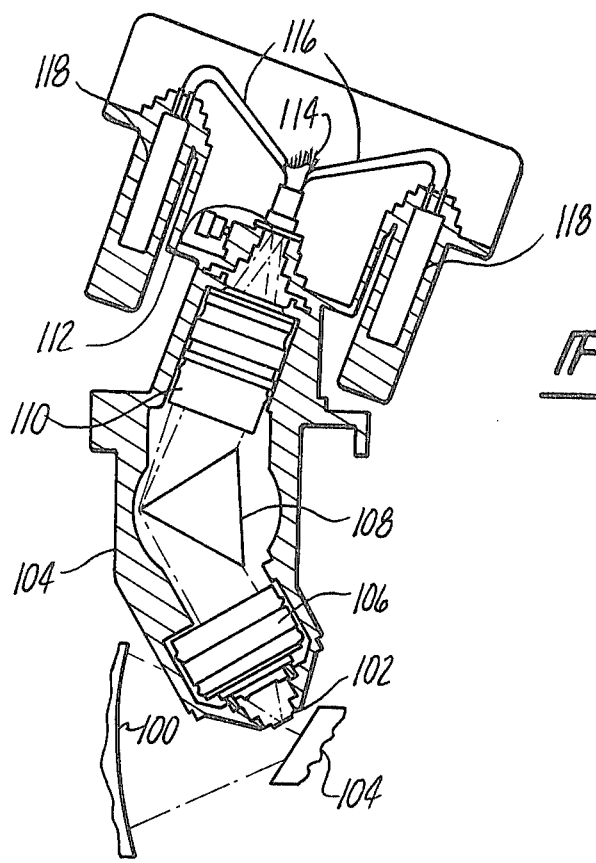
FIG. 3 is a schematic diagram of a third form of apparatus for analyzing radiation from microscopic specimens from a plurality of wavelengths.

FIG. 3 is a cross-sectional view of an alternate embodiment of apparatus for collecting the radiation emanating from a slide point irradiated with broad band radiation by a system similar to that illustrated in FIG. 2. Radiation emanating from the point is collected by a spherical primary mirror 100 and focused on an entrance slit 102 by a folding mirror 104. The entrance slit is supported on one end of a tubular optics assembly 104.

A collimating lens 106 receives a beam from the folding mirror 104 and directs it to one side of a dispersing element 108. This first output beam from the prism 108 is directed to a reimaging lens 110 supported within the optics tube 104. The reimaging lens focuses the dispersed components of the beam at various points on an end section 112 of a fiber optics bundle 114. The bundle is a cable formed of a plurality of strand groups 116 and each strand group is divided at its opposite end and connected to the photo-cathode surface of one of a plurality of photomultiplier tubes 118 arranged in a circle about the top end of the optical tube 110. The photomultipliers 118 are the equivalents of the photodetectors 88 employed in the embodiment of FIG. 2 and appropriate gating and control electronics is associated with them. Each of the photodetectors 118 generates an electric output representative of the amplitude of the radiation from the illumination point at a wavelength dependent upon positional relationship of the fiber optics strands 116 which feed the associated photomultiplier, relative to the dispersal electronics.

While the embodiments of FIGS. 1–3 are primarily intended for use with sectioned, translucent specimens, the present invention is equally applicable to the analysis of the surface characteristics of opaque specimens. In such analysis, the illuminating radiation would be directed to an elemental point on the area to be examined and the resulting radiation, either reflected or simulated, would be collected and detected.

In either form of system, using either translucent sections or an opaque specimen, it would be possible to illuminate relatively large sections of the area under consideration rather than pinpointing the incident radiation on an elemental point. The resulting radiation from an elemental point could then be analyzed by optics which would distinguish radiation emanating from that point from radiation resulting from other illuminated points within the area.

Any of the systems of the present invention could be adapted to analyze stimulated radiation, such as fluorescent radiation, rather than transmitted or reflected radiation by the inclusion of appropriate frequency selective detectors employing filters or the like.

While the embodiments of FIGS. 1–3 all employ a memory to store the collected data sets representing the radiation characteristics of elemental points at different wavelengths, alternate storage means could be provided or, alternatively, the collected information could be processed on a real time basis to make the ultimate classification, in a manner which will be subsequently described, or other forms of storage could be employed. For example, the data could be stored on either randomly or sequentially accessible magnetic devices such as tape or disc, or in bubble storage devices or the like.

After the data has been collected it must be processed to establish the most probable identity between each elemental point examined in known categories of material. After this classification process has been performed a two-dimensional mapping of the examined area will be made employing a different color or shading for each class of material identified on the area.

The classification process may be performed on a "manual" basis employing calculator or computer assistance but because of the large number of repetitive calculations involved in such computation it is preferably employed on a suitable form of special purpose computer. A variety of devices particularly adapted for this classification process have been developed to process remotely sensed data obtained from aircraft or satellites overflying the earth and collecting radiation information. A variety of such systems are disclosed, for example, in the proceedings of the Conference on Machine Processing of Remotely Sensed Data, Oct. 16–18, 1973 published by The Laboratory for Application of Remote Sensing, Purdue University, West Lafayette, Ind., 1973. Any of these systems could be adapted for analysis of data collected in connection with the practice of the present invention with varying degrees of economy.

The nature of the classification process derives from the fact that because of various statistical fluctuations in the properties of the materials being examined, and the illuminating, collecting and detection systems, the values of the elements of a data set representing the collected radiation values at the selected wavelengths for a given material will not be identical each time an elemental point of such material is examined but will vary over some range which is most easily defined in a statistical manner. Accordingly, in the classification process a collected data set, or vector, will not have a perfect match with a previously identified radiation signature of one particular material and zero comparison with similar signatures of other materials, but will have varying degrees of comparison with several previously identified material signatures. It is accordingly necessary to determine the best match on some statistical basis. To explain the nature of the classification process, consider first the elementary case of the analysis of a specimen known to consist of three separate materials wherein each elemental point is analyzed in two wavelengths. Suppose that the radiation intensity received at the scanner from each of the three materials A, B and C as a function of wavelength, is as shown by FIGS. 4a, 4b and 4c respectively.

The specific wavelengths, $\lambda_1$ and $\lambda_2$, indicated on each of the three figures correspond to the centers of the respective wavelength bands covered by the two channels of the scanner, and, therefore, for each material, the response of a given scanner channel will be proportional to the height of the material's spectral curve at the wavelength corresponding to that channel. Thus, if $x_1$ is the signal from channel 1 and $x_2$ is the signal from channel 2, the relative magnitudes of $x_1$ and $x_2$ for each of the three materials will be as indicated in FIGS. 4a, 4b and 4c.

The scanner responses for the three materials may be presented in a more compact form by considering $x_1$ and $x_2$ as the two components of a two-dimensional vector and plotting the coordinates for each material as shown in FIG. 5.

The $x_1$, $x_2$ plane shown in FIG. 5 will be referred to as signal space or "x" space. If the scanner had three channels instead of two, this space would be three dimensional, with the response of the third channel corresponding to the third dimension. If the scanner had n channels, the corresponding "x" space would be n-dimensional. Although an n-dimensional space for $n>3$ is difficult to visualize, it may be easily described and handled mathematically, as will be shown later.

As noted, because of various statistical fluctuations in the properties of the materials being scanned, and the analysis process and apparatus, the plot of $x_1$ vs. $x_2$ will not always fall into distinct points for materials A, B, and C as indicated in FIG. 5. Instead, if points for a large number of samples of these materials are plotted in u space, the points will tend to form 3 clusters as shown in FIG. 6 with each cluster corresponding to one of the three materials A, B, or C.

In general, the density of points will be greater near the center of each cluster and will become very low near the edge. Also, the cluster will tend to be elliptical rather than circular because of correlation between changes in $x_1$ and changes in $x_2$ for a given material. This means, simply, that if $x_1$ increases because of some natural occurrence, such as an increase of illumination on the area being scanned, $x_2$ will probably also increase.

The problem to be solved by the processor may be stated as follows: "Given any sample point on the $x_1$, $x_2$ plane, from what type of material, A, B, or C, was the sample obtained?" If the sample point falls near the centroid of one of the clusters of points for A, B, or C, the decision is obvious, the material belongs to the class indicated by the group near whose centroid the sample point is located.

Suppose, however, that the sample point is "e" in FIG. 6 and, thus, does not clearly belong to either A, B, or C. A decision can still be made, however, by considering the relative densities of points from material A, from material B, and from material C in the neighborhood of point e.

Assume that a large area of specimen has been scanned, and that the resulting large number of sample points has been plotted in the $x_1$, $x_2$ plane as in FIG. 6.

Let $D_A(x_1, x_2)$ be the density of sample points from material A as a function of $x_1$ and $x_2$, $D_B(x_1, x_2)$ be the density of sample points from material B, and $D_c(x_1, x_2)$ be the density of sample points from material C. Then, the total density, $D(x_1, x_2)$ at any point such as e on the plane will be given by $$D(e) = D_A(e) + D_B(e) + D_C(e)$$

where we have replaced the coordinates, $x_1$ and $x_2$, by e.

The probability that point e belongs to material A will be given by $$P_A(e) = \frac{D_A(e)}{D(e)} = \frac{D_A(e)}{D_A(e) + D_B(e) + D_C(e)}$$

Similarly, the probability that point e belongs to material B is given by $$P_B(e) = \frac{D_B(e)}{D(e)}$$

and, also $$P_C(e) = \frac{D_C(e)}{D(e)}$$

One method of deciding whether point e should be classified as belonging to material A, B, or C, would be to compute $P_A(e)$, $P_B(e)$, and $P_C(e)$ and decide in favor of the material having the highest probability.

Another method would involve choosing the material having the highest likelihood ratio. The likelihood that the sample point belongs to material A rather than any other material may be defined as $$L_A(e) = \frac{P_A(e)}{P_B(e) + P_C(e)}$$

Likelihood ratios for materials B and C may be defined in a similar manner. Thus $$L_B(e) = \frac{P_B(e)}{P_A(e) + P_C(e)}$$

and $$L_C(e) = \frac{P_C(e)}{P_A(e) + P_B(e)}$$

Deciding in favor of the material having the highest likelihood ratio is sometimes called the Maximum-Likelihood-Ratio Method. This decision can be made employing any of a variety of other statistical techniques. These "target/no target" decision criteria include the Bayesian, Minimax, Neyman-Pearson, etc. and typically result in a test of maximum likelihood.

As has been noted, a variety of these likelihood processors have been described in the technical literature. The following system, which is similar in many respects to those described, was produced at the Willow Run Laboratories of the University of Michigan and is described in Technical Report NASA CR-WRL 3165-23-T and NASA CR-2730 prepared for the National Aeronautics and Space Administration and available through National Technical Information Service (NTIS), Department of Commerce Washington, D.C. A broad description of the system is hereinafter provided. The details are described in the noted reports which are incorporated herein by reference.

The system is implemented such that it decides that a sample belongs to a given material (A, for example) if the "A" probability is greatest.

The special purpose hardware described in the reports is the classification pipeline 148 termed the MIDAS system, as shown by wide slashed lines in FIG. 7. The pipeline physically consists of a one-way data flow through the three special high speed digital processors: the DATA PATH SELECTOR 150, the PREPROCESSOR 152, and the CLASSIFIER 154. The DATA PATH SELECTOR supplies picture elements or "pixels" (each pixel can be considered a vector of up to sixteen 8 bit data bytes or channels) to the input of the pipe from one of three sources and proceeds to the PREPROCESSOR where scaling, angle correction, linear combinations, and calculations of ratios prepare the data for the key step, classification.

The actual classification of the data into categories is performed by the CLASSIFIER 154. Within the classifier the single pipeline 148 divides into four parallel pipelines 156a, 156b, 156c and 156d to perform fast simultaneous matrix multiplications. These multiplications are processed further and the results fed sequentially into a decision process wherein each former pixel is classified into one of up to 16 pre-determined categories or into a seventeenth null class. For each pixel that entered the pipeline at the DATA PATH SELECTOR, only 5 bits, a category code, emerge from the CLASSIFIER.

The CLASSIFIER performs a maximum-likelihood decision, assuming a multimodal Gaussian multi-variate distribution.

The basic calculation to be performed is $$C = \text{Max } [ln\{pr_i(X)\}] \tag{1}$$

where C is the class selected and X is the input data vector (the vector of bytes in a pixel). The probability density function is a Gaussian density function:

$$ln\{pr_i(X)\} = \frac{1}{2}\left\{ (X - M_i)^T \theta_i^{-1}(X - M_i) + ln|\theta_i| + n \ln \frac{\pi}{2} \right\} \tag{2}$$

where vector $M_i$ is the expected value of the X vector in category i, $\theta_i$ is the variance-covariance matrix for category i, and n, called the number of channels, is the dimension of X, M, and $\theta$. Define m as the number of categories into which the data can be classified, so that i ranges from 1 to m. Then formula (1) is calculated m times for each pixel, once for each of the m categories. The smaller the result of the $i^{th}$ calculation, the higher the probability that the pixel belongs to the $i^{th}$ category.

A geometrical interpretation of the decision process "C" is illustrated in FIG. 8. In this figure the vector X is comprised of 2 components, $x_1$ and $x_2$, and a plot of $ln\{pr_1(X)\} = C_1$ and $ln\{pr_2(X)\} = C_2$ is shown. These are elliptical curves in the two-dimensional plot. The constants $C_1$ or $C_2$ can be chosen by a Chi-squared test. When the computed value of the quadratic is large, the probability of the data vector originating from the distribution is small. Therefore these values are proper upper bounds. The trajectory of $ln\{pr_1(X)\} = ln\{pr_2(X)\}$ is also plotted in FIG. 8. This is the decision boundary dividing the $x_1x_2$ space into regions for which the data points are more likely to belong to category 1 or category 2 respectively.

Formula (1) consists of three additive terms. The most difficult calculation in the equation is the quadratic term $$Q_i = (X - M_i)^T \theta_i^{-1}(X - M_i) \tag{3}$$

The term $P_i = ln|\theta_i|$, is a constant for each of the m categories, is calculated prior to the classification process.

The design of the Q-calculating, or "Quadratic", portion of the CLASSIFIER follows directly from mathematical manipulation of Equation (3). The equation can be expressed in a number of ways to optimize the computation. Since the number of bits in the CLASSIFIER is limited, it is desirable to express the quadratic calculation such that the result has a limited range.

The variance-covariance matrix $\theta$ can be expressed as $$[\theta] = [\sigma][\rho][\sigma] \tag{4}$$

where $[\sigma]$ is a diagonal matrix of the standard deviation, and $[\rho]$ is the correlation matrix with all 1's on the diagonal and values of 0 to 1 off the diagonal (in some cases negative values may occur). Taking the inverse of (4) yields $$[\theta]^{-1} = \left[\frac{1}{\sigma}\right][\rho]^{-1}\left[\frac{1}{\sigma}\right] \tag{5}$$

Substitution of Eq. (5) into (3) results in $$Q = \left[\frac{X - M_i}{\sigma_i}\right]^T [\rho_i]^{-1} \left[\frac{X - M_i}{\sigma_i}\right] \tag{6}$$

The terms $(X - M)/\sigma$ can have a very wide range. However, if the range $$-8 \leq (X - M_i)/\sigma_i \leq 8 \tag{7}$$

is exceeded, the value of X for that channel is too many standard deviations from the mean to be considered for classification.

The computation of Eq. (6) could proceed in a straight-forward manner, but can be simplified somewhat due to the symmetry of the correlation matrix and its inverse. This simplification can be accomplished in more than one way. One method is as follows:

$$Q_i = [Y_i]^T = \left[\frac{X - M_i}{\sigma_i}\right]^T [B_i]^T [B_i] \left[\frac{X - M_i}{\sigma_i}\right] \tag{8}$$

where B is an upper triangular matrix formed by the decomposition of the inverse $\rho$ matrix. By calculating $$[Y_i] = [B_i]\left[\frac{X - M_i}{\sigma_i}\right] \quad (9)$$

the final matrix operation is simply $$Q = [Y_i]^T[Y_i] = \sum_{j=1}^{n} y_{ji}^2 \quad (10)$$

where the $Y_{ji}$ are the elements of the $[Y_i]$ vector.

There are four steps implied by Eqs. (8–10). These are:

(1) Substract the mean from each channel.
(2) Multiply each result by $1/\sigma$.
(3) Perform the Y matrix multiplication on each result of Step (2) to get Y's.
(4) Square each resulting Y and add the results together.

Another method for calculating Eq. (6) is to express the inverse of the correlation matrix $\rho^{-1}$ in terms of its eigenvalues and eigenvectors. We can express the correlation matrix as:

$$\rho = UAU^T \quad (11)$$

where the U matrix is comprised of eigenvectors arranged in columns, and $U^T$ is its transpose. The A matrix is the set of eigenvalues on the diagonal. Taking the inverse of the correlation matrix, it can be shown that $$\rho^{-1} = UA^{-1}U^T \quad (12)$$

which is simply to take the reciprocals of the eigenvalues and multiply by the two original eigenvector matrices. One further decomposition brings us to the desired form $$\rho^{-1} = [UA^{-\frac{1}{2}}][A^{-\frac{1}{2}}U^T] \quad (13)$$

where $A^{-\frac{1}{2}}$ means $(A^{-1})^{-\frac{1}{2}}$.

Substitution of Eq. (13) into Eq. (6) yields $$Q_i = \left(\left[\frac{X - M_i}{\sigma_i}\right]^T U_i A_i^{-\frac{1}{2}} A_i^{-\frac{1}{2}} U_i^T \left[\frac{X - M_i}{\sigma_i}\right]\right) \quad (14)$$

In this case, if a vector Y is defined as $$Y_i = A_i^{-\frac{1}{2}} U_i^T \frac{X - M_i}{\sigma_i} \quad (15)$$

and computed as such, then the final matrix operation can be performed in the same manner as in Eq. (10). The hardware required for this second calculation must perform more multiplication than in the first method. However, in order to implement the first method efficiently, a more elaborate switching scheme is needed to avoid multiplying by a large number of zeros. The details of this switching scheme were not worked out and only general consideration was given to it.

Since it appeared desirable to have the flexibility and capability to do the matrix multiplication required by either Eq. (10) or (15), the hardware was designed to do full matrix multiplication. Tests were run on over 100 spectral distributions to see if the resultant set of coefficients for either method appeared better suited to a limited-word-length multiplier. From these results it appeared that a slight advantage might be gained by using the second method.

The calculation of Q follows the four steps listed above. Precision throughout this portion of the pipeline varies from 8 to 14 bits, with the significance increasing as the data progresses from beginning to end. Q itself is a 12-bit number.

Following the calculation of Q, the 12-bit value is multiplied by a 10-bit value, $K_i^2$, a normalizing constant which is a pre-determined parameter obtained from normalizing the inverse covariance matrix, $\theta^{-1}$.

The final decision stage of the process completes the calculation of Eq. (1), by adding in the logarithm of the determinant, then decides which, if any, of the categories the pixel belongs to. This decision is made by (1) comparing the values of $ln\{pr(X)\}$ resulting from the repeated calculations of formula (1) with different M and $\theta^{-1}$ values, (2) choosing the category corresponding to the smallest calculated value, if it is small enough, and (3) outputting its 5-bit code. In the case that none of the values is small enough, a reserved code meaning "none of these" is produced. This output code is read back to the computer and stored for final display output.

The objectives of the invention in which an exclusive property or privilege is claimed are defined as follows:

1. The method of forming an image map of a specimen based on properties of points on the specimen comprising: supporting the specimen on a stage; irradiating the specimen from a source and simultaneously detecting the resulting radiation from a particular point on the specimen at a plurality of different wavelengths to generate a first set of electrical signals having values representative of properties of said point; repeatedly translating the stage relative to the source to modify the point on the specimen from which the radiation is detected to generate a plurality of additional sets of electrical signals having values representative of the properties of other points on the object; processing each of the sets of signals to compare each subset on a multi-variate statistical basis with one of a plurality of spectral signatures representing differing properties; and generating a two-dimensional array of elements, each element having a position in the array which correlates with the position of one of the points on the specimen and each element having one of a plurality of forms dependent upon the signature with which the set of signals based on that point most closely compares as a result of said multi-variate statistical comparison process.

2. The method of claim 1 wherein the specimen is sequentially irradiated with radiation of differing wavelengths to generate said set of signals.

3. The method of claim 1 wherein the object consists of a thin biological section and the resulting radiation constitutes the radiation transmitted through the section.

4. The method of claim 3 wherein the radiation transmitted through the thin biological section is polychromatic and is separated into a plurality of differing wavelengths to generate said first set of electrical signals.

5. The method of claim 1 wherein a particular point on the specimen is irradiated, the point being dependent upon the position of the stage relative to the irradiating source and the resulting radiation from the entire specimen is detected to generate said first set of electrical signals.

6. The method of claim 1 wherein the detected resulting radiation constitutes secondary radiation emitted by the specimen as a result of its radiation from said source.

7. The method of claim 1 wherein the resulting radiation constitutes radiation reflected from the specimen.

8. The method of claim 1 wherein the plurality of forms that each element of the two-dimensional array may take constitute a different color.

9. A system for analyzing the characteristics of microscopic specimens, comprising: a stage for supporting a specimen; a source of radiation directed at the specimen; a radiation sensor supported with respect to the stage to receive resultant radiation from the specimen; a signal converter operative to receive the output of the sensor and to generate signals representative of the radiation modulating characteristics of each point on the object with respect to a plurality of radiations of different wavelengths, with a set of signals representative of the radiation modulating characteristics of a particular point constituting a data vector; process means receiving the set of data vectors and performing multi-variate statistical comparison operations to segregate the data vectors into a plurality of sets each having common characteristics; and means for generating a two-dimensional display ordered in the manner of the specimen with each point depicted on the basis of the set into which it has been segregated by said processor means.

10. The system of claim 9 wherein the radiation source is polychromatic and including means for dividing the modulated radiation into a plurality of separate wavelengths and said sensor means includes a plurality of separate sensors, each positioned to measure one of said wavelengths.

11. The system of claim 10 wherein said stage is planar and is supported for motion along a line in the plane of the stage, and including means for indexing the stage to bring separate points on the specimen into position relative to said radiation.

12. The system of claim 9 wherein said radiation is polychromatic and said sensor means includes a linear array of sensors, each sensitive to a different radiation frequency, with said sensors being arrayed perpendicular to the direction of motion of the stage.

13. The system of claim 12 including a plurality of sensor groups, each group consisting of a plurality of sensor elements, each sensitive to a different radiation frequency, with the elements in the group arrayed along lines perpendicular to the direction of motion of the stage.

14. The system of claim 13 including radiation collecting means supported between the specimen and the radiation sensor, operative to collect resultant radiation from the specimen provided to the sensor.

15. The system of claim 14 wherein said resultant radiation is within the visible range and said means for collecting the radiation constitutes optical elements.

16. The system of claim 9 including means for translating the stage relative to the source of radiation to sequentially generate sets of signals representative of the radiation modulating characteristics of particular points on the specimen.

17. The system of claim 9 wherein the specimen constitutes a thin biological section and the resultant radiation constitutes radiation transmitted through the specimen whereby the radiation modulating characteristics of a particular point constitute its radiation transmission characteristics.

18. The system of claim 17 wherein the source of radiation is of visible wavelengths.

UNITED STATES PATENT AND TRADEMARK OFFICE
CERTIFICATE OF CORRECTION

PATENT NO. : 4,191,940
DATED : March 4, 1980
INVENTOR(S) : Fabian C. Polcyn et al It is certified that error appears in the above-identified patent and that said Letters Patent are hereby corrected as shown below:

Column 1, line 20, "photograhs" should be --photographs--.

Column 4, line 55, "direct" should be --detect--.

Signed and Sealed this

Tenth Day of June 1980

[SEAL]

Attest:

SIDNEY A. DIAMOND

Attesting Officer

Commissioner of Patents and Trademarks